US012766038B2

(12) United States Patent
Hallen

(10) Patent No.: US 12,766,038 B2
(45) Date of Patent: Oct. 20, 2026

(54) DUAL PORT LASER VITREOUS DISINTEGRATION DEVICE

(71) Applicant: Alcon Inc., Fribourg (CH)

(72) Inventor: Paul R. Hallen, Colleyville, TX (US)

(73) Assignee: Alcon Inc., Fribourg (CH)

( * ) Notice: Subject to any disclaimer, the term of this patent is extended or adjusted under 35 U.S.C. 154(b) by 265 days.

(21) Appl. No.: 18/505,306

(22) Filed: Nov. 9, 2023

(65) Prior Publication Data

US 2024/0189149 A1 Jun. 13, 2024

Related U.S. Application Data

(60) Provisional application No. 63/387,138, filed on Dec. 13, 2022.

(51) Int. Cl.
*A61F 9/008* (2006.01)

(52) U.S. Cl.
CPC .... *A61F 9/008* (2013.01); *A61F 2009/00874* (2013.01)

(58) Field of Classification Search
CPC ....................... A61F 9/008; A61F 2009/00874
USPC .............................................................. 606/4
See application file for complete search history.

(56) References Cited

U.S. PATENT DOCUMENTS

| | | | | |
|---|---|---|---|---|
| 5,957,914 | A | 9/1999 | Cook | |
| 8,038,692 | B2 | 10/2011 | Valencia | |
| 8,968,347 | B2 | 3/2015 | McCollam | |
| 10,238,543 | B2 | 3/2019 | Farley | |
| 10,307,290 | B2 | 6/2019 | Kern | |
| 10,376,414 | B2 | 8/2019 | Hallen | |
| 10,618,522 | B2 * | 4/2020 | Liu | B60W 40/08 |
| 10,729,582 | B2 | 8/2020 | Biancalana | |
| 10,874,552 | B2 * | 12/2020 | Wells | A61F 9/00754 |
| 10,918,522 | B2 * | 2/2021 | Bacher | G02B 6/3518 |
| 11,583,441 | B2 | 2/2023 | Lopez et al. | |
| 2006/0206050 | A1 | 9/2006 | Chon | |
| 2010/0106054 | A1 * | 4/2010 | Hangai | A61F 9/00821 600/566 |
| 2015/0182756 | A1 * | 7/2015 | Peyman | A61K 48/0033 604/20 |
| 2019/0008680 | A1 | 1/2019 | Jochinsen | |
| 2019/0201238 | A1 * | 7/2019 | Bacher | A61F 9/008 |
| 2021/0290438 | A1 * | 9/2021 | Hallen | A61F 9/00836 |

FOREIGN PATENT DOCUMENTS

WO WO-9852502 A1 * 11/1998 ......... A61F 9/00754

* cited by examiner

*Primary Examiner* — Ahmed M Farah

(74) *Attorney, Agent, or Firm* — Patterson + Sheridan, LLP

(57) ABSTRACT

A vitreous disintegration device with multiple intake ports and a laser for vitreous disintegrating. The probe includes a needle to accommodate the ports for a more continuous and fluidic uptake of vitreous from an eye of a patient. Additionally, the use of a laser may be employed to disintegrate the vitreous in a manner that avoids blocking of ports and thus, further promoting the fluidic uptake. The laser may reach the ports at the channel at substantially the same time or in succession. Further, the use of a laser for the disintegrating means that cutter vibrations may be reduced.

18 Claims, 5 Drawing Sheets

DUAL PORT LASER VITREOUS DISINTEGRATION DEVICE

BACKGROUND

Over the years, many dramatic advancements in the field of eye surgery have taken place. Often, in retina procedures, a vitrectomy may be included in at least part of the procedure. Vitrectomy is the removal of some or all of the vitreous humor from a patient's eye. In some cases, where the surgery was limited to removal of clouded vitreous humor, the vitrectomy may constitute the majority of the procedure. However, a vitrectomy may accompany surgery to repair a retina, to address a macular pucker or a host of other issues.

The vitreous humor itself is a clear gel that may be removed by an elongated probe when inserted through a pre-placed cannula at the eye. More specifically, the probe includes a tubular implement with a lumen or central channel for removal of the vitreous humor. Of course, removal of the vitreous humor requires greater care than simply applying a vacuum through the channel of the probe. This is because the vitreous humor includes a fibrous matrix of collagen fibrils. That is, the fibrous nature of the gel is such that a vacuum pull on the gel into the probe might translate into a pull on the retina, optic nerve or other delicate eye structures.

In order to address this issue, vitrectomy probes are configured to cut vitreous humor as it is drawn into the channel of the probe. In this way, a continuous fibrous pull on the gel-like substance does not translate into a pull on delicate eye structures. In some vitrectomy cutters, the fluid uptake of the vitreous humor may be interrupted by the reciprocating of the cutter which closes the uptake port with each cut. This means that the flow of uptake may not be continuous, even where some probes which may achieve 5-10,000 cuts per minute or more.

SUMMARY

A vitreous disintegration device is disclosed. In one embodiment, the probe includes a tubular implement with proximal and distal ports for the uptake of vitreous humor into a channel defined by the implement. The probe further includes a laser emitting device coupled to the implement to deliver a laser through the channel and adjacent the ports for incising of the vitreous humor therein.

DETAILED DESCRIPTION

In the following description, numerous details are set forth to provide an understanding of the present disclosure. However, it will be understood by those skilled in the art that the embodiments described may be practiced without these particular details. Further, numerous variations or modifications may be employed which remain contemplated by the embodiments as specifically described.

Embodiments are described with reference to certain types of vitreous disintegration surgical procedures. In particular, a procedure in which vitreous humor is removed/disintegrated to address vitreous hemorrhage is illustrated. However, tools and techniques detailed herein may be employed in a variety of other manners. For example, embodiments of a vitreous disintegration device as detailed herein may be utilized to address retinal detachments, macular pucker, macular holes, vitreous floaters, diabetic retinopathy or a variety of other eye conditions. Regardless, so long as the vitreous disintegration device incorporates dual port vitreous humor uptake in combination with laser incising of the vitreous humor, appreciable benefit may be realized.

Figure 1:
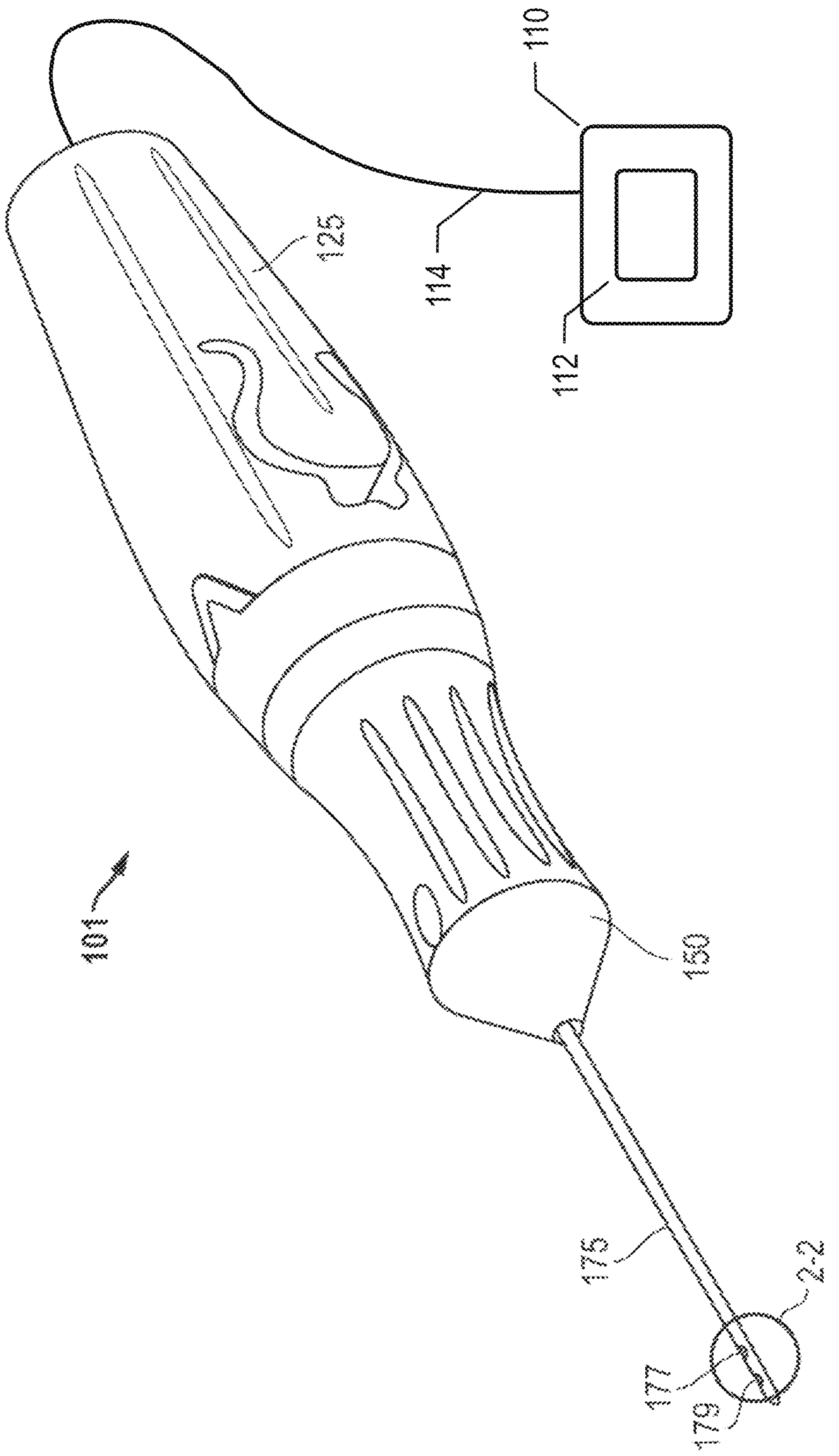
FIG. 1 is a perspective view of an embodiment of a dual port laser vitreous disintegration device.

Referring now to FIG. 1, a perspective view of an embodiment of a dual port laser vitreous disintegration device 101 (also referred to as a probe 101) is illustrated. The probe 101 may include features such as a shell or support 125 as well as a housing 150 which allows the probe to rest at the purlicue at the base of the surgeon's index finger close to the thumb during a vitrectomy. Similarly, a probe implement or needle 175 is provided to facilitate access to the interior of an eye 450 of a patient as detailed below (see FIG. 4). However, more notably, the needle 175 is constructed with multiple ports 177, 179 for the uptake of vitreous humor or other eye material and particulate. In the embodiment shown, two ports 177, 179 are illustrated. However, in other embodiments, more than two ports may be utilized 177, 179. A laser emitting device 112 may be located in a surgical console 110 optically coupled to the support 125 of the vitreous disintegration device 101 using an optical cable 114.

By utilizing multiple ports 177, 179 in combination with the manner of incising of the vitreous humor, the probe 101 may facilitate the uptake of vitreous humor and other eye material in a more fluidic fashion. That is, for a conventional "vit-probe", a single port in combination with an interior cutter leads to a mechanical reciprocation that results in periodic chopping or cutting of vitreous in combination with repeated port closure. Thus, the uptake of eye material through the needle 175 may be less fluidic and choppy. This means that for a conventional vitrectomy, intermittent pulling on delicate eye features may occur when removing vitreous. However, as detailed below, these risks are substantially eliminated by the multiple port embodiment illustrated, particularly when combined with incising of the vitreous in a manner that does not require port closure.

Figure 2:
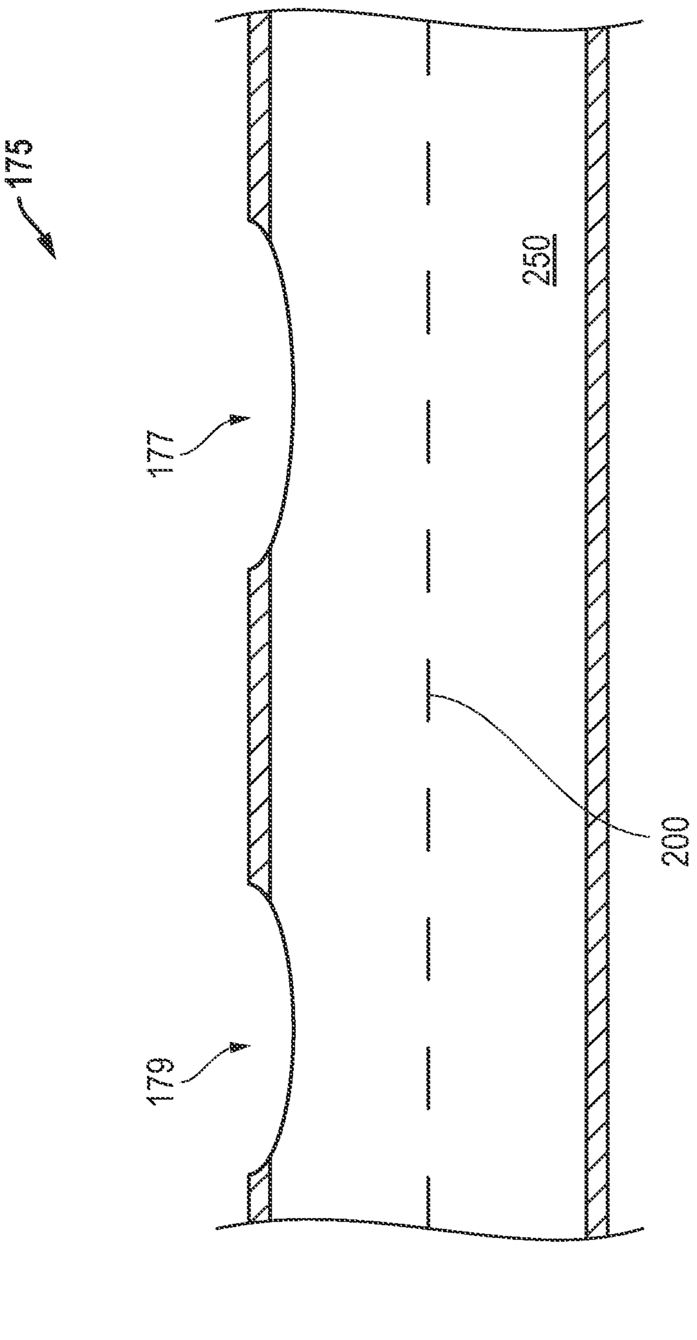
FIG. 2 is an enlarged cross-sectional view of a needle for the vitreous disintegration device taken from 2-2 of FIG. 1.
Figure 4:
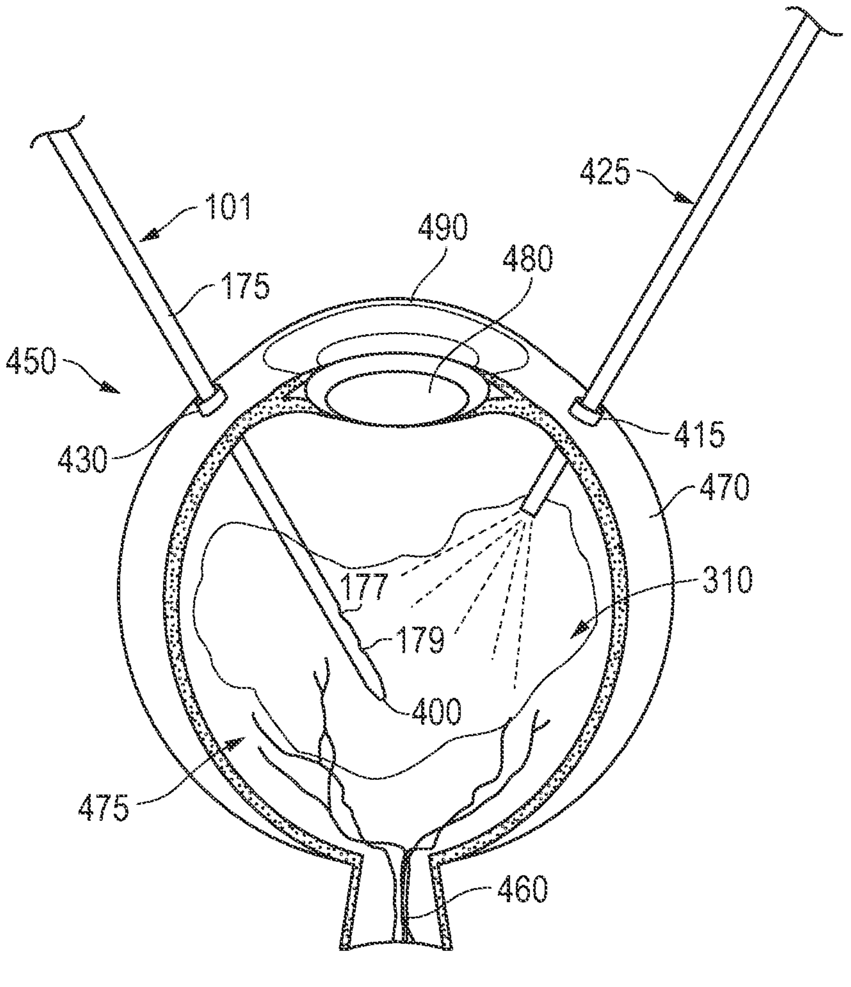
FIG. 4 is an overview of an embodiment of a vitrectomy surgery performed with the vitreous disintegration device of FIG. 1.

Referring now to FIG. 2, an enlarged cross-sectional view of a needle 175 for the vitreous disintegration device 101 taken from 2-2 of FIG. 1 is illustrated. In this view, a channel 250 is shown into which vitreous humor and other substances may be drawn during a surgical procedure with the needle 175 inserted into the eye 450 of a patient as illustrated in FIG. 4. In this view it is evident how the ports 177, 179 may each serve to allow for the influx of the noted substances.

Continuing with reference to FIG. 2, unlike a mechanical chopper vitrectomy probe, the needle 175 is not outfitted with a cutter in the channel 250. As a result, the ports 177, 179 are not obstructed by the cutter during the noted intake of vitreous and other eye material. Instead, a laser 200 is utilized that is directed through the channel 250 in order to cut/disintegrate vitreous type material as detailed further below.

It is worth noting that the ports 177, 179 for the illustrated embodiment are axially aligned with one another. That is, they are located at the same side of the needle 175 and along the same axis at the exterior surface thereof. This may help to enhance the fluidic uptake of vitreous type material as described below. However, as a practical matter, this may also serve to aid the surgeon in directing the ports 177, 179 to a particular eye location of interest without introducing the potential added challenge of the ports 177, 179 being in significantly different circumferential positions relative the location of interest. Of course, depending on the nature of the application, in other embodiments there may be a benefit to utilizing different circumferential needle positions for the ports 177, 179, for example where the needle 175 is inserted into an injury site for vitreous or other eye injury related material.

Figure 3A:
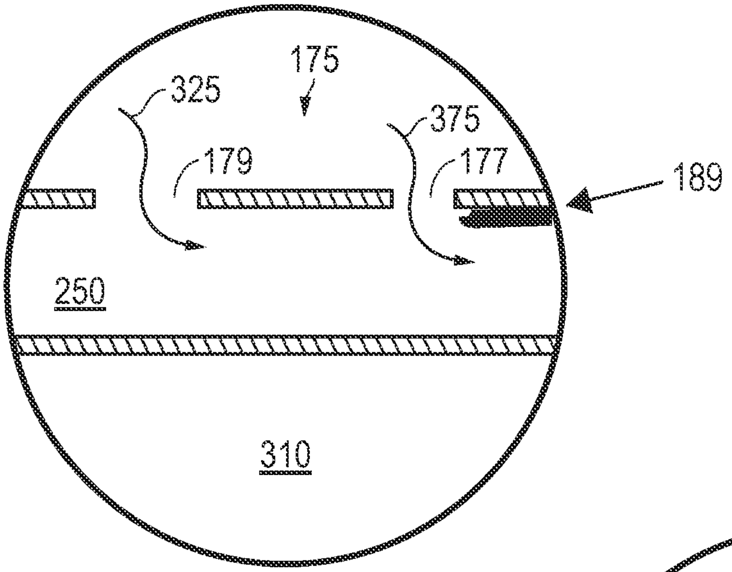
FIG. 3A is a side cross-sectional view of the needle of FIG. 2 during initial uptake of vitreous humor during a vitrectomy as illustrated in FIG. 4.

Referring now to FIG. 3A, a side cross-sectional view of the needle 175 of FIG. 2 is illustrated during initial uptake of vitreous humor during a vitrectomy as illustrated in FIG. 4. More specifically, two different fluid flow paths 325, 375 are provided through the ports 177, 179 and into the channel 250. Thus, an influx of fluid material from the interior 310 of the eye of the patient may proceed.

Figure 3B:
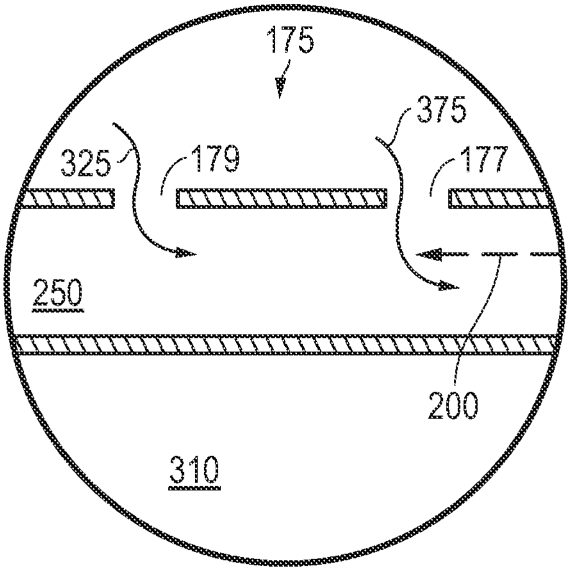
FIG. 3B is a side cross-sectional view of the needle of FIG. 2 during proximal laser incising of the vitreous humor uptake illustrated in FIG. 3A.

Referring now to FIG. 3B, a side cross-sectional view of the needle 175 of FIG. 2 is shown during proximal laser incising/disintegration. Specifically, a laser 200 directed from a proximal location (e.g., from a laser in an attached surgical console or from a laser within a handpiece of the vitreous disintegration device) is transmitted through the channel 250 (e.g., through air or an optical fiber aligned with the channel), eventually reaching the vitreous flow 375 at the more proximal of the ports 177. Thus, as with a interior cutter, the vitreous or other material intake at the proximal port 177 is incised/disintegrated. In this way, fibrous pulling by the depicted intake 375 may be substantially reduced.

In some embodiments, the laser 200 may include a biocompatible pico- or femto-laser. In some embodiments, the laser 200 is pulsated in a non-continuous fashion. For example, the laser 200 may be set to operate at 50-90K (50,000-90,000) pulses per minute. In this way, a tailored or controlled incising/disintegration may proceed. However, the pulsating is rapid enough to present a substantially continuous beam of the laser 200. Thus, the incised/disintegrated intake 375 may proceed in a substantially pull-free and fluidic manner. Of course, the laser 200 may be presented through the channel 250 in a more continuous fashion as well.

Figure 3C:
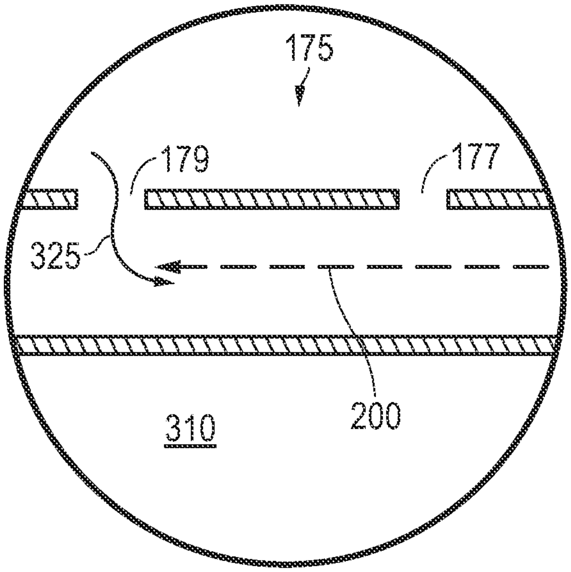
FIG. 3C is a side cross-sectional view of the needle of FIG. 2 during distal incising of the vitreous humor uptake illustrated in FIG. 3B.

Referring now to FIG. 3C, a side cross-sectional view of the needle 175 of FIG. 2 is illustrated during distal incising 325 of the vitreous humor uptake through the distal port 179. In this view, the proximal intake 375 illustrated in FIG. 3B has been incised/disintegrated and does not present any significant obstacle to the laser 200 in reaching the more distal vitreous intake 325 (see FIG. 3B). Indeed, depending on a host of factors, the laser 200 may cut through both port intakes 325, 375 at substantially the same time. However, in circumstances where the more proximal intake 375 as shown in FIG. 3B presents an obstacle to the laser 200, incising/disintegration of this intake 375 allows for the laser 200 to reach the more distal intake 325 for incising/disintegration there as well. Regardless, the intake of vitreous may remain substantially continuous and fluidic due to the use of multiple ports 177, 179 which are not closed during the intake process as described. In some embodiments, the laser may be delivered in front of the ports through open air or an optical fiber (e.g., optical fiber 189) located proximate the proximal most port 177. In some embodiments, the laser may be delivered through multiple optical fibers (e.g., one optical fiber terminating adjacent to each port 177, 179). Further, while two ports 177, 179 are illustrated, additional ports may be included which may also have adjacent laser pulses to cut vitreous entering the additional ports.

FIG. 4 is an overview of an embodiment of a vitrectomy surgery performed with the vitreous disintegration device 101 of FIG. 1. During the procedure, a beveled end 400 of the needle 175 of the vitreous disintegration device 101 is inserted through a preplaced cannula 430 and directed toward a region 310 where vitreous humor is to be removed. Specifically, as described above, a suction is applied and the ports 177, 179 are used for the uptake of the vitreous humor or other substances. For example, in the procedure illustrated, a hemorrhage may be taking place in the region 310 such that blood is drawn into the ports 177, 179 along with the vitreous humor.

As also described above, and with added reference to FIG. 2, a reciprocating cutter within the needle 175 has been replaced with a laser 200 to facilitate this delicate procedure. This means that the ports 177, 179 are each able to remain open throughout the procedure so as to promote a more consistent fluidic flow of vitreous and other substance uptake from the region 310. An added benefit of utilizing the laser 200 in place of a reciprocating cutter is the fact that the incising/disintegration would be substantially vibration and noise-free. That is, vibrations resulting from cutter reciprocation are eliminated entirely. Thus, any interference or audible vibrating nuisance to the surgeon performing the procedure in this regard are reduced.

Continuing with reference to FIG. 4, the surgery illustrated includes the probe 101 and a light instrument 425 reaching into the eye 450 through cannulas 415, 430 positioned in an offset manner at the sclera 470. In this way, the more delicate cornea 490 and lens 480 may be avoided. By the same token, the optic nerve 460 and retina 475 are also quite delicate. Therefore, given that the needle 175 is capable of reaching these delicate features at the back of the eye 450, minimizing pull thereon by maintaining a more fluidic uptake of vitreous as described above may be of substantial benefit. Similarly, the eliminating of potential distracting vibrations to the surgeon as described herein may also be significantly beneficial.

Figure 5:
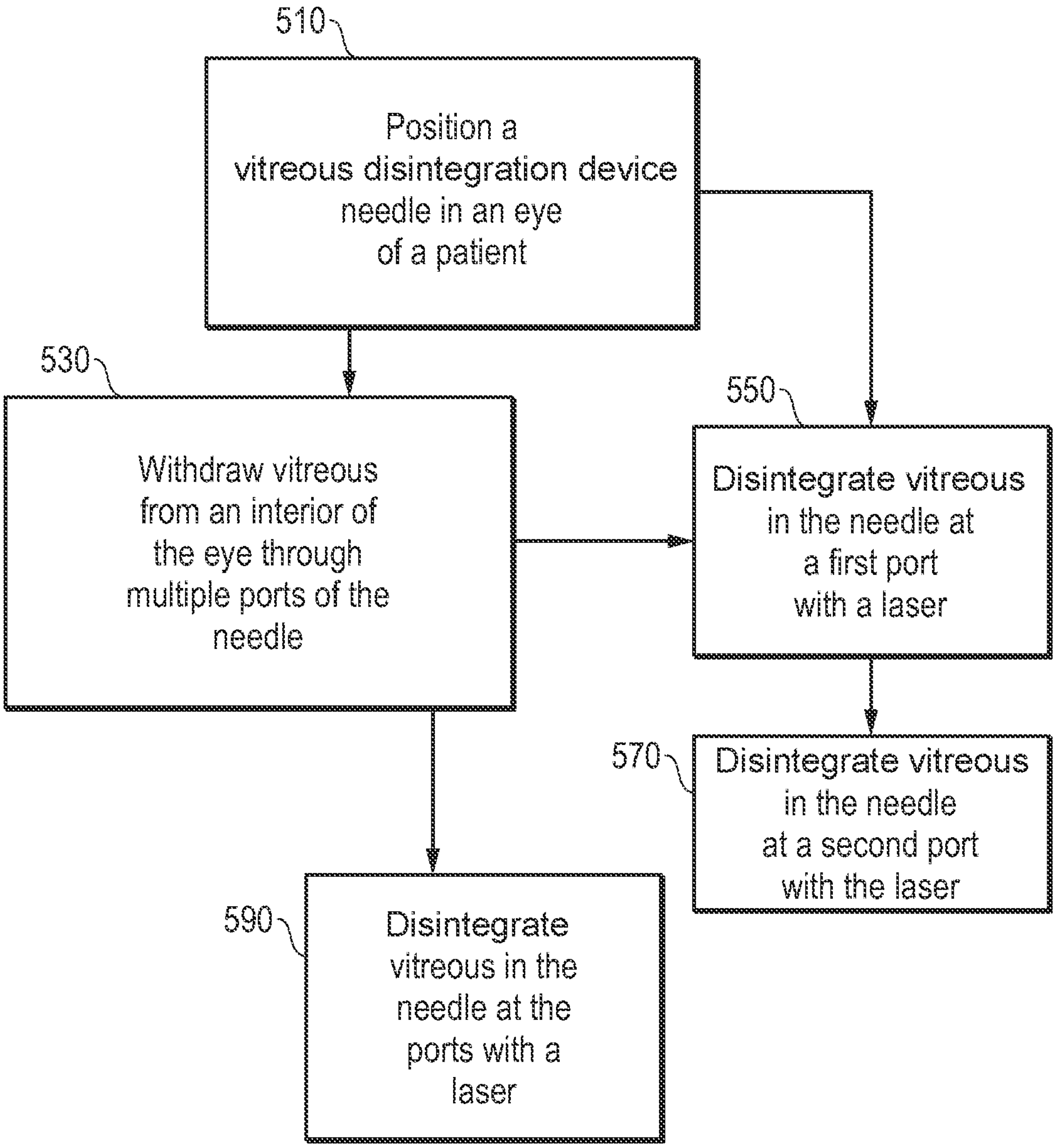
FIG. 5 is a flow-chart summarizing an embodiment of employing a dual port laser vitreous disintegration device in a surgical procedure.

Referring now to FIG. 5, a flow-chart is shown summarizing an embodiment of employing a dual port laser vitreous disintegration device in a surgical procedure. As indicated at 510, a vitreous disintegration device needle may be inserted into the eye of a patient for a vitrectomy procedure. Thus, vitreous and other substances may be withdrawn from the interior of the eye. Indeed, as indicated at 530, the vitreous may be withdrawn through multiple ports. Further, a laser may be utilized to incise/disintegrate the vitreous within the needle at the location of the ports (see 590). As a result, a cutter or other implement which might close off the ports is avoided so that the vitreous may be pulled in continuously. Additionally, where the incising/disintegrating vitreous itself presents an obstacle to the path of the laser, incising/disintegration may occur at a first (more proximal) port (see 550) and then at a second (see 570) and so forth, depending on the number of ports utilized. All in all, this means that there may be substantially reduced interruption of vitreous uptake and therefore, a more fluidlike, continuous withdrawal of the vitreous. This may provide for an enhanced withdrawal with less pull on delicate eye structures by the incoming vitreous.

Embodiments described hereinabove include a vitreous disintegration device with capacity to achieve a more fluidic uptake of vitreous and other substances from an eye of a patient. Once more, this is achieved in a manner that avoids port closure without increasing the likelihood of vitreous pull on delicate eye structures. Thus, overall safety and efficiency for vitrectomy procedures may be realized.

The preceding description has been presented with reference to presently preferred embodiments. However, other embodiments and/or features of the embodiments disclosed but not detailed hereinabove may be employed. Furthermore, persons skilled in the art and technology to which these embodiments pertain will appreciate that still other alterations and changes in the described structures and methods of operation may be practiced without meaningfully departing from the principle and scope of these embodiments. Additionally, the foregoing description should not be read as pertaining only to the precise structures described and shown in the accompanying drawings, but rather should be read as consistent with and as support for the following claims, which are to have their fullest and fairest scope.

The invention claimed is:

1. A method of performing a vitrectomy, the method comprising:

advancing an implement of a vitreous disintegration device into an eye of a patient;

withdrawing vitreous through at least two ports of the implement and into a channel thereof; and disintegrating the vitreous with a laser in the channel, wherein the disintegrating of the vitreous occurs in one of a vibration-free manner and a noise-free manner.

2. The method of claim 1, wherein the at least two ports are axially aligned on the implement.

3. The method of claim 2, wherein the disintegrating comprises incising vitreous in the channel at the at least two ports in a simultaneous manner.

4. The method of claim 2, wherein the disintegrating comprises incising of vitreous in the channel at a first proximal port of the at least two ports in advance of incising of vitreous at a second distal port of the at least two ports.

5. The method of claim 1, wherein the withdrawing of the vitreous through the at least two ports is unobstructed.

6. The method of claim 1, wherein the laser is a pulsating laser operating at between 50,000 and 90,000 pulses per minute.

7. A method of performing a vitrectomy, the method comprising:

advancing an implement of a vitreous disintegration device into an eye of a patient;

withdrawing vitreous through at least two ports of the implement and into a channel thereof; and disintegrating the vitreous with a laser in the channel, wherein the disintegrating comprises incising vitreous in the channel at the at least two ports in a simultaneous manner.

8. The method of claim 7, wherein the at least two ports are axially aligned on the implement.

9. The method of claim 8, wherein the disintegrating comprises incising of vitreous in the channel at a first proximal port of the at least two ports in advance of incising of vitreous at a second distal port of the at least two ports.

10. The method of claim 7, wherein the withdrawing of the vitreous through the at least two ports is unobstructed.

11. The method of claim 7, wherein the laser is a pulsating laser operating at between 50,000 and 90,000 pulses per minute.

12. The method of claim 7, wherein the disintegrating of the vitreous occurs in one of a substantially vibration-free and a substantially noise-free manner.

13. A method of performing a vitrectomy, the method comprising:

advancing an implement of a vitreous disintegration device into an eye of a patient;

withdrawing vitreous through at least two ports of the implement and into a channel thereof; and disintegrating the vitreous with a laser in the channel, wherein the disintegrating comprises incising of vitreous in the channel at a first proximal port of the at least two ports in advance of incising of vitreous at a second distal port of the at least two ports.

14. The method of claim 13, wherein the at least two ports are axially aligned on the implement.

15. The method of claim 14, wherein the disintegrating comprises incising vitreous in the channel at the at least two ports in a simultaneous manner.

16. The method of claim 13, wherein the withdrawing of the vitreous through the at least two ports is unobstructed.

17. The method of claim 13, wherein the laser is a pulsating laser operating at between 50,000 and 90,000 pulses per minute.

18. The method of claim 13, wherein the disintegrating of the vitreous occurs in one of a substantially vibration-free and a substantially noise-free manner.

* * * * *